US00PP09679P

United States Patent [19]

Knaap

[11] Patent Number: Plant 9,679

[45] Date of Patent: Oct. 29, 1996

[54] FICUS PLANT NAMED CURLY

[76] Inventor: Wim V. D. Knaap, Oudecampsweg 10, 2678 KN, De Lier, Netherlands

[21] Appl. No.: 496,292

[22] Filed: Jun. 29, 1995

[51] Int. Cl.[6] ..... A01H 5/00

[52] U.S. Cl. ..... Plt./88.9

[58] Field of Search ..... Plt./88.9

[56] References Cited

U.S. PATENT DOCUMENTS

P.P. 6,460 12/1988 Simoens ..... Plt./88.9

P.P. 7,736 12/1991 Deroose ..... Plt./88.9

P.P. 8,902 9/1994 Denis ..... Plt./88.9

P.P. 9,491 3/1996 van Geest ..... Plt./88.9

*Primary Examiner*—James R. Feyrer

*Attorney, Agent, or Firm*—Foley & Lardner

[57] ABSTRACT

A *Ficus benjamina* plant named Curly, particularly characterized by its compact branched habit, its green and cream white unpredictable chimeral variegation, its variety of leaf shapes, and its white to burgundy stems and petioles.

2 Drawing Sheets

The present invention comprises a new and distinct cultivar of *Ficus benjamina,* known by the cultivar name Curly.

Curly is a mutation discovered by the inventor Wim V. D. Knaap in February 1988 in greenhouse in De Lier, Holland. The new cultivar was disovered among plants of the unpatented parent cultivar Starlight, and was recognized due to its unusual colors and variegation.

The first act of asexual reproduction of Curly was accomplished when cuttings were taken by the inventor in February 1988 in De Leir, Holland. Horticultural examination of plants of Curly has demonstrated that the combination of characteristics as herein disclosed for the new cultivar are firmly fixed and are retained through successive generations of asexual reproduction.

Curly has not been observed under all possible environmental conditions. The phenotype may vary significantly with variations in environment such as temperature, light intensity, and daylength, without, however, any variance in genotype. The following observations, measurements and values describe plants grown in Homestead, Fla. under field conditions which closely approximate those commonly used in horticultural practice.

The following traits have been repeatedly observed to be characteristics which in combination particulary distinquish Curly as a unique new cultivar.

1. The variegation is highly variable from one leaf to the next with respect to location on the leaf, extent of the leaf surface involved, and pattern.

2. When variegation is present, it appears to cause the leaf to become curled, puckered, or misshapen in a myriad of ways.

3. The variegation may or may not appear on every leaf. Often, individual leaves may be entirely green or entirely white.

4. The upper leaf surface variegation pattern is often different from the lower leaf surface variegation pattern.

5. Despite the variability in variegation pattern and color, plants of Curly consistently display this trait. The new cultivar is characteristically consistently variable in expression and a stable cultivar.

6. The stems and petioles of Curly are white when in active growth, often changing to burgundy red, particularly under high light conditions.

7. The variable variegation pattern of Curly, together with its variety of leaf shapes and sizes, compact branched habit, and colorful petioles and stems, is a striking and unique combination.

All color references below are measured against The Royal Horticultural Society Color Chart. Colors are as closely approximate as possible. Color may vary somewhat depending on horticultural practices such as light level and fertilization rate, among others.

The accompanying color photographic drawings illustrate a typical specimen plant of Curly, with photographic color depicting true colors to the extent possible with reproductions of this type.

The photograph on Sheet 1 comprises a top perspective view of Ficus Curly in a 25.5 cm pot approximately 32 weeks after planting a single rooted cutting.

The photograph on Sheet 2 illustrates the detail in the variegation pattern and stem color which are characteristic of Curly.

Origin: Mutation discovered among plantings of the parent cultivar Starlight.

Classification: *Ficus benjamina,* c.v. Curly.

Propagation: By cuttings.

Plant description: When a rooted cutting is grown in a 25.5 cm pot for 8 months under appropriate growing conditions, Curly is approximately 47 cm to 51 cm from the soil surface to the top of the leaf canopy, and approximately 56 cm to 60 cm in width.

*Habit.*—The plant is generally an upright compact woody shrub. The growth habit and shape are typical of *Ficus benjamina.* The main trunk has many ascending branches arising at approximately 45 degrees from the stem axis, becoming nearly horizontal to the stem axis near the tip.

*Stems and trunks.*—New shoots are 155A in color, changing to 183D. Mature wood is browner than, but closest to, 199A.

*Leaves.*—Form: The leaves are arranged alternately along the stems. There is approximately 2.1 cm to 3.0 cm between leaves along the stem. The leaves are generally elliptical with an obtuse base and a rather long acuminate tip. However, the occurrence of variegation on the leaf may dramatically change the leaf shape, often to a more lanceolate form. The leaves are often distorted, twisted, puckered, or wavy, depending on the extent and location of variegation. Size: Approximately 5.7 cm to 7.1 cm long, and approximately 1.6 cm to 3.5 cm wide. Margin: The leaf margin is typically wavy, and distorted. Texture: The leaf surface is glossy. The nature of the variegation is such as to cause the erratic absence or presence of entire cell layers within the lamina of the leaf, causing sunken and raised areas on both the upper and lower leaf surface. Petiole: Approximately 1.1 cm to 1.5 cm long, approximately 1.1 mm thick; color is 155A, often changing to 183D when exposed to intense light. Veins: The midrib is prominent, recessed on the upper surface, and protruding on the lower surface. The midrib is typically 144A in color on the upper leaf surface, although its color is often the same as the variegation pattern present. The midrib on the lower leaf surface is 155A, often tinged with 183D. The primary veins are recessed in the leaf lamina, and are the same color as the leaf tissue surrounding them. Variegation: Chimeral and irregular in appearance. No two leaves are even remotely similar in pattern. The variegation consists primarily of cream white, or blotches of cream white diffused with dark green specks. Dark green areas of the leaf are often marked with areas of light green. Color: The following colors may be found in variable amount, and in vaiable combination on any leaf. New Leaves: Upper Surface: Significa..t colors are 137A, 146C, and 158C and 150D. Lower Surface: Significant colors are 146B-C, 158C. Mature Leaves: Upper Surface: Significant colors are darker and green than, but closest to, 137A, 146B, and 4D. Lower Surface: Significant colors are 146B-C and 158B-C.

Inflorescence and reproductive organs: Flowers and fruit have not been observed in detail but are typical for the species.

Roots: Dark wiry roots with fine laterals, terrestrial, and aerial roots present.

It is claimed:

1. A new and distinct cultivar of *Ficus benjamina* plant named Curly, as illustrated and described.

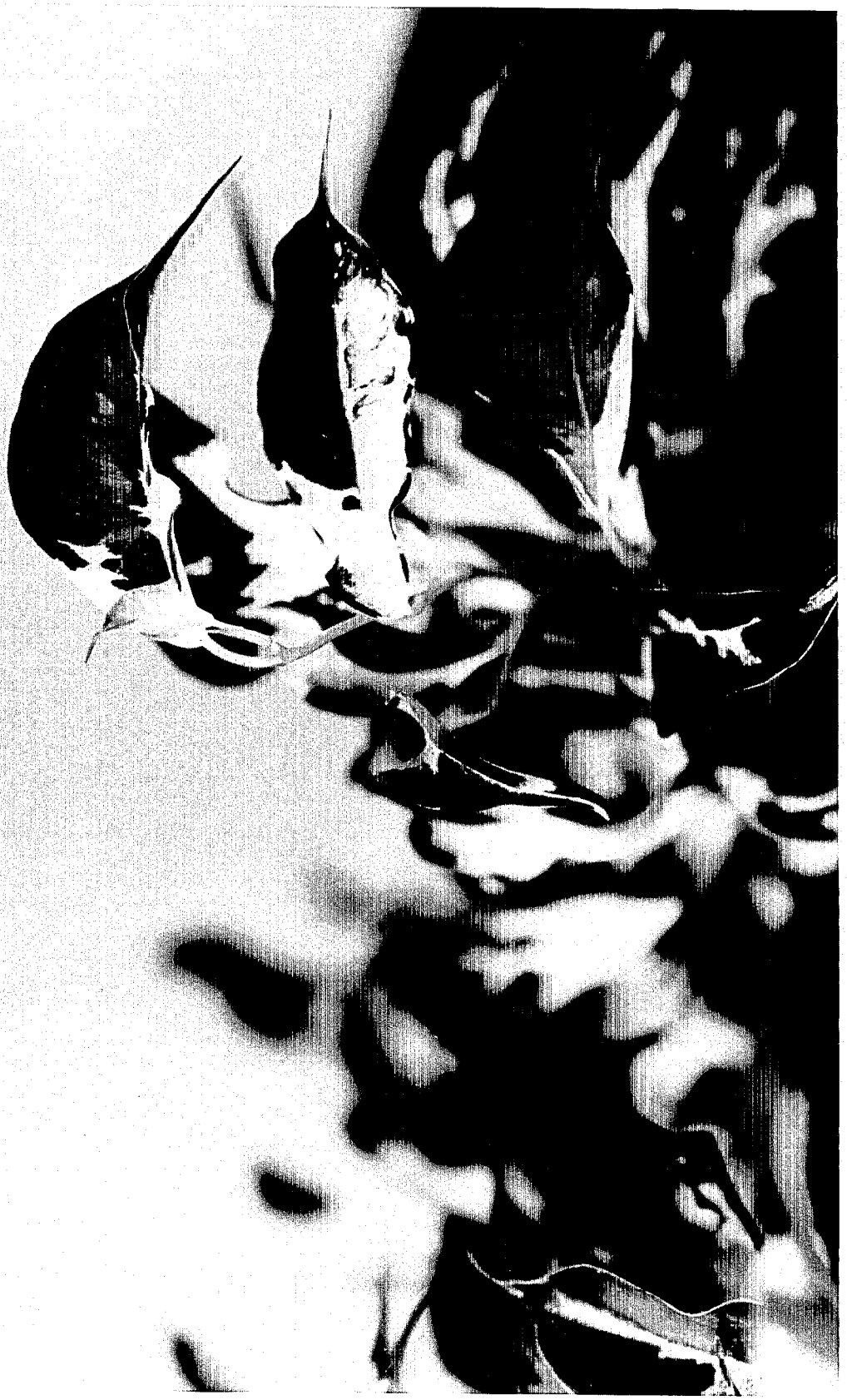

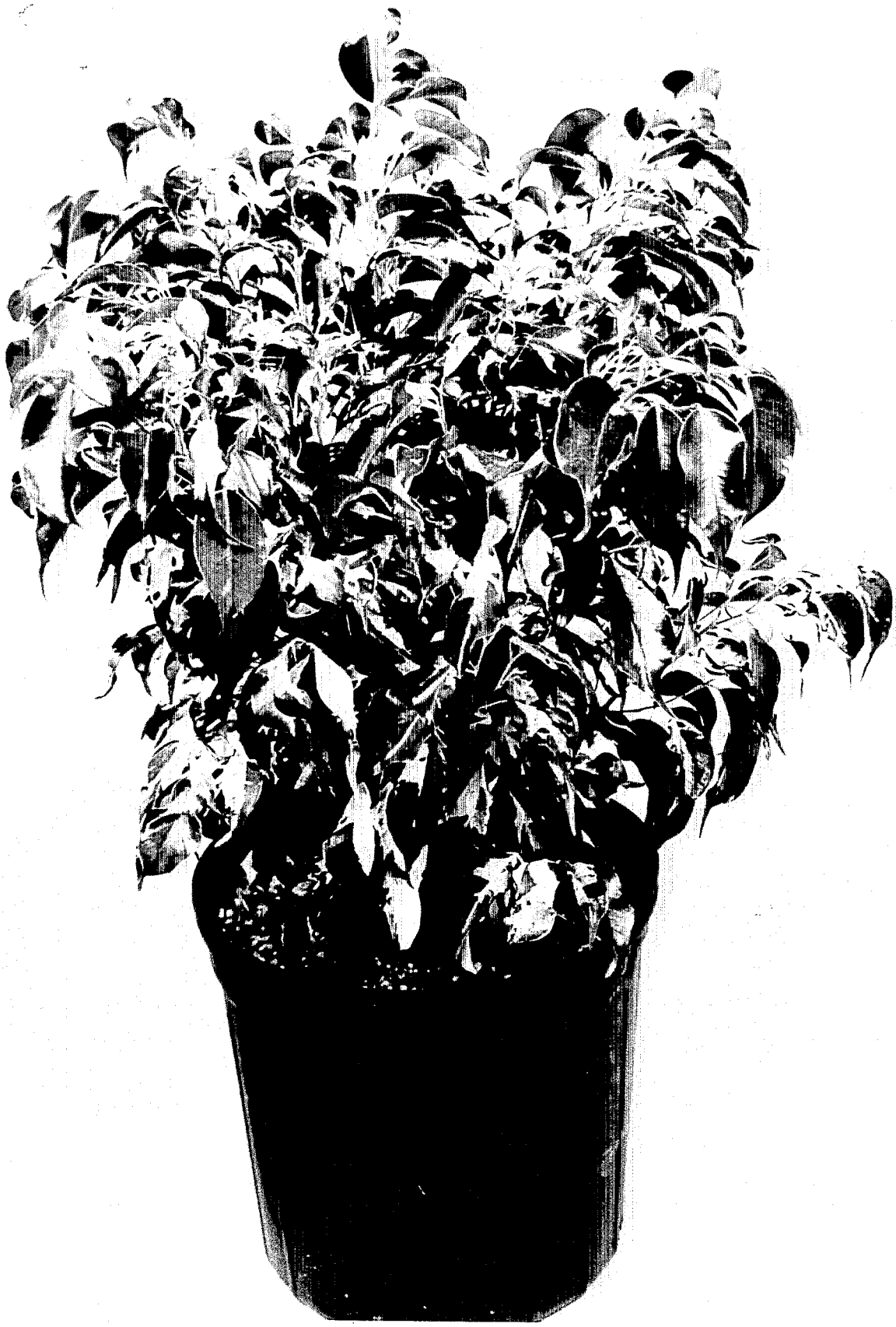

* * * * *